(12) United States Patent
Ohayon et al.

(10) Patent No.: US 10,007,983 B2
(45) Date of Patent: Jun. 26, 2018

(54) IMAGE PROCESSING METHOD BASED ON THE FINITE ELEMENT METHOD FOR DIRECTLY SOLVING INVERSE PROBLEMS IN STRUCTURAL MECHANICS

(71) Applicant: UNIVERSITE GRENOBLE ALPES, St. Martin d'Hères (FR)

(72) Inventors: Jacques Ohayon, Tresserve (FR); Adeline Bouvier, Saint-Martin d'Heres (FR); Guy Cloutier, Repentigny (CA)

(73) Assignee: Universite Grenoble Alpes, St. Martin d'Heres (FR)

( * ) Notice: Subject to any disclaimer, the term of this patent is extended or adjusted under 35 U.S.C. 154(b) by 160 days.

(21) Appl. No.: 14/915,690

(22) PCT Filed: Sep. 3, 2014

(86) PCT No.: PCT/FR2014/052172
§ 371 (c)(1),
(2) Date: Mar. 1, 2016

(87) PCT Pub. No.: WO2015/033058
PCT Pub. Date: Mar. 12, 2015

(65) Prior Publication Data
US 2016/0196645 A1 Jul. 7, 2016

(30) Foreign Application Priority Data

Sep. 3, 2013 (FR) ..................... 13 58425

(51) Int. Cl.
*G06T 7/00* (2017.01)
*A61B 8/12* (2006.01)
(Continued)

(52) U.S. Cl.
CPC .......... *G06T 7/0012* (2013.01); *A61B 8/0891* (2013.01); *A61B 8/12* (2013.01);
(Continued)

(58) Field of Classification Search
USPC ................................... 382/128, 131
See application file for complete search history.

(56) References Cited

U.S. PATENT DOCUMENTS 6,165,128 A  12/2000  Cespedes et al.
6,277,074 B1 *  8/2001  Chaturvedi .......... A61B 8/0833
                                              600/437
(Continued)

OTHER PUBLICATIONS

Bouvier, Adeline, et al.; "A Direct Vulnerable Atherosclerotic Plaque Elasticity Reconstruction Method Based on an Original Material-Finite Element Formulation: Theoretical Framework," Physics in Medicine and Biology, vol. 58, No. 23, Dec. 7, 2013, pp. 8457-8476.
(Continued)

*Primary Examiner* — Ishrat I Sherali
(74) *Attorney, Agent, or Firm* — Harness, Dickey & Pierce, PLC

(57) ABSTRACT

The present disclosure relates to an image processing method including the following steps: receiving a deformation or displacement image; defining a meshing of the deformation image; assigning a respective pair of unknown variables to each node of the meshing; detecting one (or more) node(s) located at the boundary between two different materials of the body studied; enriching the node(s) detected; calculating a basic matrix for each basic cell of the meshing; assembling the basic matrixes in order to obtain an overall structural matrix; calculating a resilience image of the body based on the overall structural matrix.

8 Claims, 2 Drawing Sheets

(51) Int. Cl.
*G06F 17/50* (2006.01)
*G06K 9/46* (2006.01)
*G06K 9/52* (2006.01)
*G06T 7/11* (2017.01)
*G06T 7/13* (2017.01)
*A61B 8/08* (2006.01)

(52) U.S. Cl.
CPC ............ *A61B 8/485* (2013.01); *A61B 8/5215* (2013.01); *G06F 17/5018* (2013.01); *G06K 9/4604* (2013.01); *G06K 9/52* (2013.01); *G06T 7/11* (2017.01); *G06T 7/13* (2017.01); *A61B 8/085* (2013.01); *G06K 2009/4666* (2013.01); *G06T 2207/10132* (2013.01); *G06T 2207/20112* (2013.01)

(56) References Cited

U.S. PATENT DOCUMENTS

| | | | |
|---|---|---|---|
| 7,318,804 B2 * | 1/2008 | Weitzel | A61B 8/08 600/438 |
| 7,338,452 B2 | 3/2008 | Shiina et al. | |
| 8,394,026 B2 * | 3/2013 | Eskandari | A61B 8/00 600/438 |
| 8,660,326 B2 | 2/2014 | Ohayon et al. | |
| 8,965,487 B2 * | 2/2015 | Bouma | A61B 5/0059 600/476 |
| 9,554,777 B2 * | 1/2017 | Kim | G01N 29/0654 |
| 2004/0009459 A1 * | 1/2004 | Anderson | G06F 19/3406 434/262 |
| 2010/0160778 A1 | 6/2010 | Eskandari et al. | |
| 2011/0093243 A1 * | 4/2011 | Tawhai | G06F 17/5018 703/2 |
| 2011/0282182 A1 * | 11/2011 | Ohayon | G06T 7/0012 600/407 |

OTHER PUBLICATIONS

Céspedes, E. I., et al., "Intraluminal Ultrasonic Palpation: Assessment of Local and Cross-Sectional Tissue Stiffness," Ultrasound in Med. & Biol., vol. 26, No. 3, 2000, pp. 385-396.

Deleaval, Flavien, et al., "The Intravascular Ultrasound Elasticity-Palpography Technique Revisited: A Reliable Tool for the in vivo Detection of Vulnerable Coronary Atherosclerotic Plaques," Ultrasound in Med. & Biol., vol. 39, No. 8, Mar. 1, 2013, pp. 1469-1481.

Doyley, M. M., et al.; "Evaluation of an Iterative Reconstruction Method for Quantitative Elastography," Phys. Med. Biol., 45, 2000, pp. 1521-1540.

Doyley, M. M.; "Model-Based Elastography: A Survey of Approaches to the Inverse Elasticity Problem," Phys. Med. Biol., 57, Jan. 6, 2012, pp. R35-R73.

Le Floch'H, Simon, et al.; "On the Potential of a New IVUS Elasticity Modulus Imaging Appraoch for Detecting Vulernable Atherosclerotic Coronary Plaques: in vitro Vessel Phantom Study," Phys. Med. Biol., Sep. 8, 2010, pp. 5701-5721.

Le Floc'H, Simon, et al.: "Vulerable Atherosclerotic Plaque Elasticity Reconstruction Based on a Segmentation-Driven Optimization Procedure Using Strain Measurements: Theoretical Framework," IEEE Transactions on Medical Imagining, vol. 28, No. 7, Jul. 2009, pp. 1126-1137.

Moës, Nicolas, et al.; "A Finite Element Method for Crack Growth Without Remeshing," International Journal for Numerical Methods in Engineering, vol. 46, Sep. 10, 1999, pp. 131-150.

Oberai, Assad A., et al.; "Solution of Inverse Problems in Elasticity Imaging Using the Adjoint Method," Inverse Problems, 19, 2003, pp. 297-313.

Zhu, Yanning, et al.; "A Finite-Element Approach for Young's Modulus Reconstruction," IEEE Transactions on Medical Imaging, vol. 22, No. 7, Jul. 2003, pp. 890-901.

* cited by examiner

IMAGE PROCESSING METHOD BASED ON THE FINITE ELEMENT METHOD FOR DIRECTLY SOLVING INVERSE PROBLEMS IN STRUCTURAL MECHANICS

CROSS-REFERENCE TO RELATED APPLICATIONS

This application is a National Phase Entry of International Patent Application No. PCT/FR2014/052172, filed on Sep. 3, 2014, which claims priority to French Patent Application Serial No. 1358425, filed on Sep. 3, 2013, both of which are incorporated by reference herein.

TECHNICAL FIELD

The present invention relates to the general technical field of image processing in structural mechanics, and notably of image processing for solving inverse problems in linear elasticity. A non-limiting exemplary application of the present invention relates to the field of reconstructing elasticity of atherosclerotic lesions for estimating a risk of failure of an atheromatous plaque. However, it is quite obvious for one skilled in the art that the present invention is not limited to this particular application.

BACKGROUND

1. Consequence of a Failure of an Atheromatous Plaque

Atheroma or atherosclerosis corresponds to a rearrangement of the tunica intima of the arteries of large and medium caliber (aorta, coronary arteries, carotids, cerebral arteries, arteries of the lower limbs, etc.) by segmental accumulation of lipids, complex carbohydrates, blood and blood products, adipose tissues, calcium deposits and other minerals within the intima (which is the internal layer of the vessel). This vascular pathology is generally with slow progression (over decades). It may be stabilized and not exhibit any notable risk for the patient. But it may also degenerate into an unstable form leading to breakage of the plaque and, in a few days, may cause cardiovascular or cerebral strokes (CVA), either deadly or morbidly.

Indeed, the breakage of a plaque puts its contents in contact with the blood conveyed by the artery, which may cause the formation of a thrombus. The latter perturbs blood flow in the affected artery. It may also be detached and transported by the blood flow, and in the most severe cases, completely block the lumen of the artery, stopping irrigation of the post-lesion region and cause its ischemia. The characterization of the mechanical properties of the tissues (i.e. of their elasticity) has a fundamental benefit in medical diagnostics, notably for estimating a risk of breakage of an atheromatous plaque.

2. Measurement of the Thickness of the Fibrous Cap for Diagnosing Risky Atherosclerosis Plaques In order to allow estimation of a risk of failure of an atheromatous plaque, several intravascular imaging techniques have been developed. These are notably:
  Intravascular echography (IVUS),
  Optical coherence tomography (OCT), and
  Magnetic resonance imaging (IV-MRI)
These different imaging techniques give the possibility of obtaining an image of the atheromatous plaque and of measuring the thickness of the fibrous cap of the latter. However, only knowing the thickness of the fibrous cap is not a sufficient indicator of stability of the plaque for estimating a risk of failure of an atheromatous plaque.

3. Estimation of the Amplitude of the Stress at the Fibrous Cap in Order to Detect a Failure Risk From prior work it was possible to establish that the amplitude of the maximum stress at the fibrous cap (or "PCS", acronym of "Peak Cap Stress") is a good biomechanical indicator of the vulnerability of an atheromatous plaque. However, quantifying the amplitude of the maximum stress at the fibrous cap (PCS) in vivo remains a challenge since such a mechanical stress in the fibrous cap not only depends on the morphology of the atheromatous plaque, but also on the mechanical properties of the components of the plaque, and notably on the inclusions contained in the latter. Although several methods have been developed for extracting the distributions of the deformations in an atheromatous plaque, the complexity of the geometries of the atherosclerosis plaques do not give the possibility of directly inferring the mechanical properties of the plaque from the knowledge of the deformations.

Over the last 20 years, a new medical imaging method was developed: this is ultrasonic elastography. Based on the same principles as palpation, elastography locally studies the elastic behavior of a medium under the action of a stress. This study is based on the analysis of radiofrequency ultrasonic signals acquired before and after applying a stress, or acquired for different stress levels.

4. Prior Art Known in the Field of Elastography 4.1 Elastography

Ultrasonic elastography consists of estimating the elasticity of a soft tissue from techniques for processing sequences of backscattered echographic images by the latter when it deforms. The processing of these images allows determination of the distribution of the rigidity/elasticity of this tissue.

4.2 Direct Problem and Inverse Problem in Elastography

In standard structure computing, the direct problem consists of predicting the stresses within a tissue, by knowing the distribution of its elasticity. More specifically, knowing:
  the structure of the tissue (i.e. its geometry in any point),
  the rigidity/elasticity of the different materials making up the tissue, and
  the load on the tissue (i.e. the field of external stresses exerted on the tissue),
it is possible to determine a displacement field in any point of the tissue and thus trace back the spatial distribution of the stresses knowing the elastic behavior laws of the media.

Oppositely, the inverse problem consists of determining the elasticity of a tissue, given the displacements from the ultrasonic signals which it emits in different compression conditions. More specifically, knowing:
  the structure of the tissue (obtained by using echographic image processing methods),
  the evolving loading of the tissue (obtained by measuring external stresses exerted on the tissue), and
  the field of displacement or deformations in any point of the tissue (obtained by comparing in every point representative ultrasonic images of the ultrasonic signals acquired for different loading levels),
it is possible to determine the rigidity/elasticity of the different materials making up the tissue.

4.3 Known Methods for Determining the Rigidity/Elasticity of a Tissue

Several methods based on the finite element method have been developed for estimating a map of vascular elasticity from the estimation of the deformation field inside an atherosclerotic lesion obtained by intravascular imaging. The finite element method in mechanics consists of producing a meshing of an image of a body to be studied. The meshing allows spatial discretization of the body. This meshing consists of elementary cells also called adjacent "meshes" (triangular, polygonal, square, etc.) each consisting of nodes and of edges delimiting a portion of the body (see for example document US 2010/0160778 A1).

Zhu et al.

Zhu et al. (2003) developed a direct method for reconstruction based on the finite element method. This method uses assumptions on the mechanical properties so as to obtain a direct relationship between the deformation field and Young's modulus. Notably, it is assumed in this method that the mechanical properties of the plaque are constant for each elementary cell. In spite of its robustness, this method has a very long computation time because of the large number of elementary cells during the examination of a very heterogeneous atherosclerotic plaque.

Oberai et al. (2003)

In order to surmount this limitation, Oberai et al. (2003) proposed a method for reconstructing an elasticity map (for all the cases of inverse problems in structural mechanics) in which not only the force and the displacements are considered as nodal variables of the cells, but also the Young modulus and the Poisson coefficient. Said approach has the name of "Nodal Mechanical Properties" and the acronym of "NMP". Thus, for a given elementary cell, Oberai et al. propose the consideration of the elasticity variables at the nodes of the cell, and inference of the elasticities within these elementary cells by interpolation by using a polynomial interpolation function.

A drawback of this method is that it does not give the possibility of considering the discontinuities of the material in the atheromatous plaque. Indeed, the polynomial interpolation functions require continuity of the interpolated variable. Thus, the spatial shape functions used do not allow characterization of a heterogeneous atheromatous plaque having high discontinuities of materials between the different inclusions of the atheromatous plaque.

LeFloc'h et al. (2009)

LeFloc'h et al. (2009) developed an iterative method for reconstruction known under the name of "IMOD" (acronym of "Imaging MODulography"). The iterative reconstruction methods generally consist of:

assigning elasticity values to the different components/inclusions of an atheromatous plaque.

estimating a deformation field from assigned elasticity values, comparing the computed deformation field to the deformation field as measured by intravascular imaging, and repeating the preceding steps until the difference between the calculated deformation field and the measured deformation field is less than a threshold.

The IMOD method (proposed by LeFloc'h et al.) comprises a pre-conditioning step using criteria for detecting heterogeneities so as to automatically identify the contours of all the components of the atheromatous plaque. The use of such criteria is carried out by using a parametric model controlled by one segmentation by watershed.

In spite of the efficiency and the robustness of the IMOD approach, this method does not allow a real reconstruction of the elasticity in real time. Indeed, this method—like all the iterative reconstruction methods—requires a very long computing time (of the order of several minutes) because of the large number of re-iteration of the computing steps (assignment, estimation, comparison) to be applied for obtaining a vascular elasticity map illustrating the local distribution of Young's modulus of the atherosclerotic plaques.

SUMMARY

An object of the present invention is to propose a reconstruction method giving the possibility of overcoming at least one of the aforementioned drawbacks. Notably, an object of the present invention is to propose a real time reconstruction method of an elasticity image of a body—such as an atheromatous plaque—from radiofrequency ultrasonic signals acquired before and after applying a load, or acquired for different loading levels.

For this purpose, the invention proposes an image processing method allowing the formation of an elasticity image of a body depending on the material(s) making up said body, characterized in that the method comprises the steps:

receiving a deformation image illustrating a displacement or deformation field of the points of the body versus a pressure difference in the body, defining a meshing of the deformation image, said meshing step applying a finite element method, the meshing consisting of a plurality of elementary cells (or meshes) each delimiting a same material and each including at least three nodes, each node belonging to one or several adjacent cells of the meshing, assigning to each node i of the meshing a pair of unknown nodal variables (corresponding to the Lamé coefficients ($\lambda_i$, $\mu_i$) or to Young's modulus and to the Poisson coefficient ($E_i$, $v_i$)), each pair being representative of elastic properties to be determined detecting at least one node common to at least two adjacent elementary cells delimiting different materials, enriching said and at least one detected common node, said enrichment step consisting of replacing the pair of unknown variables assigned to said detected common node with at least two pairs of enrichment unknown variables, each pair of enrichment unknown variables of the detected common node being assigned to a respective elementary cell from among said at least two adjacent elementary cells delimiting different materials, calculating an elementary matrix for each elementary cell of the meshing so as to obtain a plurality of elementary matrices, the elementary matrix of an elementary cell being computed by considering pairs of unknown variables assigned to said elementary cell, and pairs of unknown enrichment variables assigned to said elementary cell, assembling the elementary matrices from the plurality of elementary matrices in order to obtain a structural matrix, and calculating an elasticity image of the body from the deformation image and from the structural matrix.

Thus, the present invention proposes a new direct formulation by finite elements for solving the inverse problem in linear elasticity. This formulation is based on the introduction of new interpolation functions which give the possibility of taking into account the discontinuities of material inside the studied body. This new method may advantageously be applied in any piece of software for structural calculations with finite elements in linear elasticity.

Preferred but non-limiting aspects of the method according to the invention are the following:

The method further comprises, prior to the step consisting of defining a meshing, a step consisting of segmenting the deformation image so as to obtain a segmented deformation image consisting of a plurality of regions representative of areas of the body assume to be in different materials;

the step consisting of defining a meshing is applied on the segmented deformation image, the dimensions and positions of the cells of the meshing being determined according to the positions and dimensions of the regions of the segmented deformation image;

the step consisting of computing an elasticity image comprises the resolution of the following matrix equation:

$$\{R\}=([Q']^T[Q'])^{-1}[Q']^T\{F'\}$$

wherein:

[Q'] represents the reduced structural matrix, and $[Q']^T$ its transposed,

{R} represents the matrix of the field of the elasticities of the body at the nodes, {F'} represents the reduced matrix of the field of forces applied to the nodes;

the step consisting of enriching a detected common node comprises the replacement of the pair of unknown variables assigned to said detected common node with n pairs of enrichment unknown variables, n corresponding to the number of different materials at the boundary of which said common node is located.

The invention also relates to an image processing system allowing the formation of an elasticity image of a body depending on the material(s) making up said body, characterized in that the system comprises:

a receiver for receiving a deformation image illustrating a displacement field of the points of the body depending on a pressure difference in the body, a processor configured for:

defining a meshing of the deformation image by applying a finite element method, the meshing consisting of a plurality of elementary cells each delimiting a same material and each including at least three nodes, each node belonging to one or several adjacent cells of the meshing, assigning to each node i of the meshing a pair of unknown nodal variables ($\lambda_i$, $\mu_i$), each pair being representative of elastic properties to be determined, detecting at least one node common to at least two adjacent elementary cells delimiting the different materials, enriching said and at least one detected common node, the enrichment consisting of replacing the pair of unknown variables assigned to said detected common node with at least two pairs of enrichment unknown variables, each pair of enrichment unknown variables of the detected common node being assigned to a respective elementary cell from among said at least two adjacent elementary cells delimiting different materials, calculating an elementary matrix for each elementary cell of the meshing so as to obtain a plurality of elementary matrices, the elementary matrix of an elementary cell being computed by taking into account pairs of unknown variables assigned to said elementary cell, and pairs of unknown variables assigned to said elementary cell, assembling the elementary matrices from the plurality of elementary matrices for obtaining a structural matrix, and calculating an elasticity image of the body from the deformation image and from the structural matrix.

Preferred but non-limiting aspects of the system according to the invention are the following:

the system further comprises a display device for displaying the computed elasticity image;

the processor is configured for applying the steps of the method described above.

The invention also relates to a computer program product including a program code recorded on a data medium legible by a computer for executing the method described above when the computer program is applied to a computer so as to be executed.

BRIEF DESCRIPTION OF THE DRAWINGS

Other features and advantages of the invention will still emerge from the following description, which is purely illustrative and non-limiting and should be read with reference to the appended drawings, wherein.

DETAILED DESCRIPTION

1. Introduction

Figure 1:
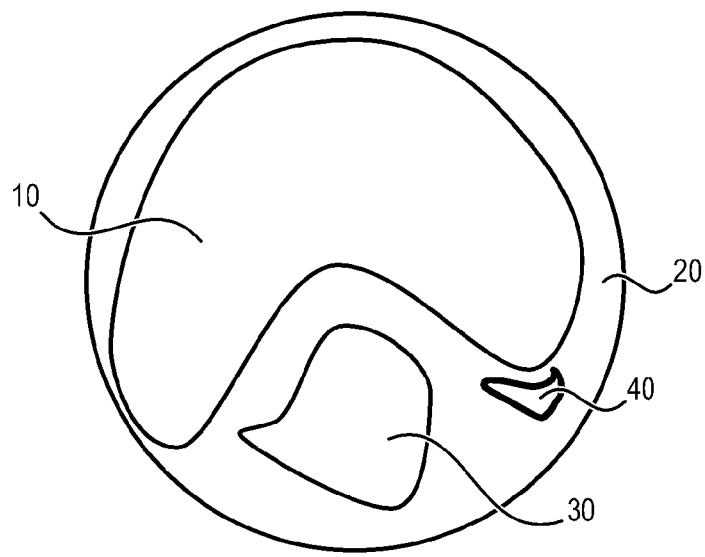
FIG. 1 illustrates an atheromatous plaque.

As indicated in the prior art presentation part, Oberai et al. proposed a reconstruction method by finite elements for solving an inverse problem in structural mechanics. This method—which allows reconstruction of an image representing the different elasticities of a body—is original in that not only the force and the displacements are considered as nodal variables, but also the Young modulus and the Poisson coefficient (or which amounts to the same both Lamé coefficients). However, a drawback of this method relates to the use of continuous spatial shape functions. This does not give the possibility of characterizing the bodies having high discontinuities of the materials.

Moreover, as this reconstruction method is iterative, it does not allow reconstruction of an image representing the different elasticities of a body in real time. The present invention was therefore developed for allowing a reconstruction in real time of an image representing the different elasticities of a body consisting of at least two areas having a material discontinuity.

2. Field of Application of the Method

An exemplary method according to the invention will now be described in more detail. This method is notably applicable to the determination of an elasticity map of a body including at least one inclusion and at least one cavity, the different material(s) making up the body being substantially incompressible.

In the following, the present invention will be described with reference to providing in real time a piece of information relating to the elasticity of the different inclusions contained in a body. More specifically, the present invention will be described with reference to a method for generating an elasticity image of Young's modulus of a heterogeneous deformable structure surrounding a cavity. Notably, the method will be described with reference to the study of a vessel with atheromatous plaque.

However, it is quite obvious for one skilled in the art that the method according to the invention may be applied:

to other types of bodies either including a cavity or not, such as the heart, the pancreas, the liver, the prostate, the breast, . . . or to any type of industrial structure either containing or not a cavity and where the deformation has to be quantified, in order to simultaneously reconstruct the mappings of the Young modulus E and of the Poisson coefficient ν (or which amounts to the same, the mappings of both Lamé coefficients λ and μ)

3. The Principle of the Method

The novel method described hereafter is based on a finite element method (FEM) analysis giving the possibility of obtaining a meshing of the studied body. The meshing consists of a plurality of cells, the contours of each cell delimiting a material with its own mechanical properties. This method was developed by using the approach of the nodal mechanical properties (NMP) for the material.

In order to model the discontinuities between the cells of the meshing, the Extended Finite Element Method (or "XFEM") was adapted to the NMP approach (NMP-XFEM). The XFEM method is today the most reliable for treating cracking in finite elements and managing the discontinuities in displacements (see for example the study entitled "A FINITE ELEMENT METHOD FOR CRACK GROWTH WITHOUT REMESHING", Nicolas MOES, International Journal for Numerical Methods in Engineering, Vol. 46, pages 131-150, Sep. 10, 1999). The presence of singularities (cracks, perforations, etc.) strongly degrades the convergence of the Finite Element Method (FEM), and therefore it is not sufficient to strongly refine the meshing in proximity to the singularities in order to obtain a good solution. Different approaches have been proposed for overcoming this problem, most relying on the introduction at the displacements of functions with a shape capable of representing the behavior of a cracked body at the crack. The XFEM method as for it proposes an enrichment of the nodes (i.e. doubling the nodes) located on the crack. The adaptation of this method to the NMP approach is novel and gives the possibility of handling the discontinuities of the materials within the studied body. The method for direct reconstruction of the elasticity of an atheromatous plaque according to the invention was applied to six coronary lesions of patients imaged in vivo by intravascular ultrasound echography (IVUS).

4. Generalities Relative to the Method

An exemplary atheromatous plaque is illustrated in FIG. 1. This plaque is a sectional artery portion. It comprises an inner wall 10 defining and delimiting a cavity inside which flows blood, and an outer wall 20 defining the external surface of the artery. The plaque also comprises a space 30 filled with a segmental accumulation of lipids (also called necrotic core). The atheromatous plaque may also comprise other inclusions such as a calcified region 40. Thus, an atheromatous plaque generally comprises one or several inclusions (lipid, calcium, etc.) in different materials.

Figure 2:
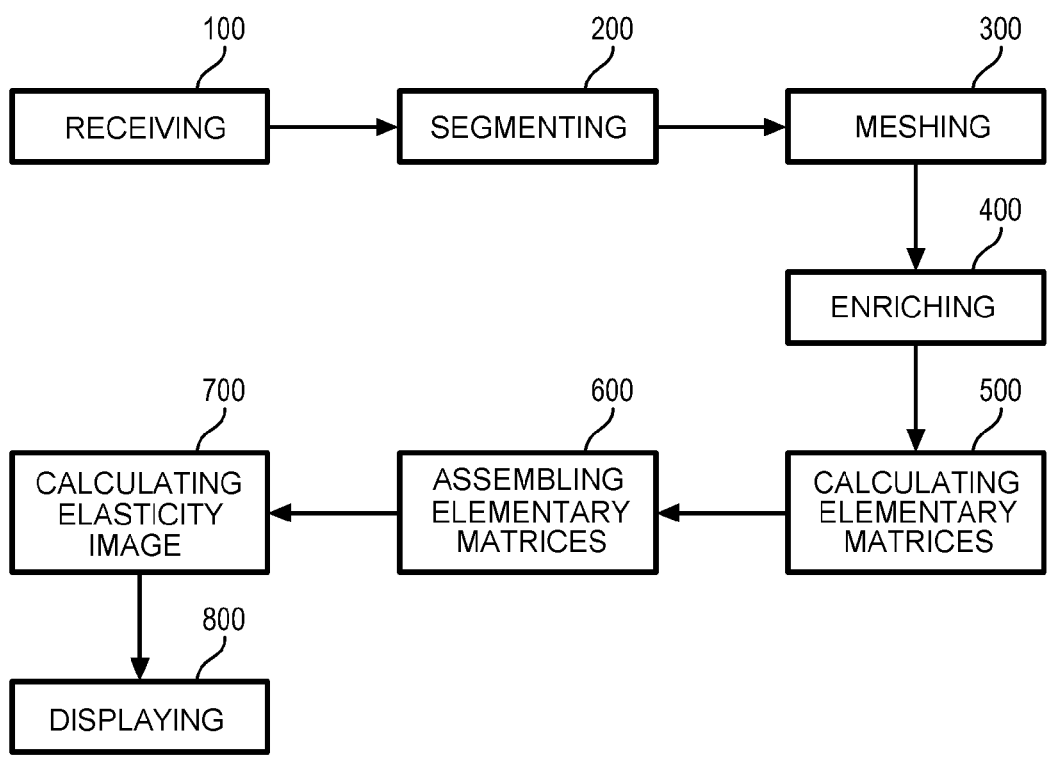
FIG. 2 illustrates the steps of the method according to the invention.

With reference to FIG. 2, the method according to the invention comprises the following steps:

receiving (step 100) a deformation image illustrating a displacement or deformation field of the points of the body as a function of a pressure difference in the body, optionally, segmenting (step 200) the deformation image, defining a meshing (step 300) of the deformation image, assigning to each node i of the meshing a pair of unknown variables $(\lambda_i, \mu_i)$ (or $(E_i, \nu_i)$) representative of the elastic properties of the body, detecting one or several nodes localized at the boundary between two or several different materials of the body, enriching (step 400) the detected node(s), computing an elementary matrix (step 500) for each elementary cell of the meshing, assembling (step 600) elementary matrices for obtaining a matrix with a global structure, calculating (step 700) an elasticity image of the body from the global structure matrix.

4.1 Receiving a Mapping Image of Deformation/Displacement of the Points Making Up the Body to be Studied As indicated above, the method comprises a step 100 for receiving a deformation image—a so called "deformation elastogram"—illustrating a deformation field of the points of the body according to a pressure difference in the body. The deformation elastogram represents the internal deformations which result from the compression of the analyzed body—here a vascular blood tissue—depending on the blood pressure. The deformation elastogram may be obtained by any method known to one skilled in the art.

For example, deformation elastogram may be obtained in the following way. An ultrasonic wave is introduced into an artery of a patient at an artery portion which one wishes to analyze. A sequence of ultrasonic images of the portion of the artery is acquired while the arterial tissue becomes compressed/expands under the effect of the heartbeat. The deformation elastogram is obtained by studying the kinetics of the time sequence of ultrasonic images.

Notably, the kinetic study may comprise steps:

comparing two different images of the artery portion acquired at two distinct instants of a heartbeat cycle, said different images being acquired for two different loads exerted on the artery portion, determining a map of the displacements by comparing the position of each of the points or pixels between two different images, determining an arterial pressure difference between both different images by subtracting the arterial load pressures measured during the acquisition of said different images.

A deformation image—or deformation elastogram—is thus obtained of the artery portion on the one hand, and the pressure difference having given the possibility of obtaining this deformation image on the other hand. Both of these pieces of information (i.e. mapping of the displacements/deformations of the analyzed body, and pressure difference associated with the mappings of the displacements/deformations) are useful for applying a subsequent step for determining the elasticity of the internal wall of the cavity of the body.

4.2 Segmentation

The step for segmenting the deformation image gives the possibility of obtaining a segmented deformation image comprising a plurality of regions delimited by their contour. Each region of the plurality of regions is representative of an area of the body to be studied, and more specifically of an area of the body assumed to be in a material different from that of the area(s) which surround it. A first region for example delimits a lipid inclusion of the atheromatous plaque, a second region delimits a calcium inclusion, etc. More specifically, the segmentation step allows detection of the contours of the different inclusions of the atheromatous plaque, and notably:

the inner contour of the artery portion, and representative of the inner wall 10 defining a cavity inside which the blood flows, the outer contour of the artery portion, and representative of the outer wall 20 defining the external surface of the artery, the outer contours of the various inclusions 30, 40 of the atheromatous plaque.

The segmentation step allows a significant reduction in the amount of data contained in the deformation image, and removes the irrelevant information for applying subsequent steps of the method, while retaining the significant structural properties of the deformation image. The segmentation step may use a segmentation technique per watershed, or any other segmentation technique known to one skilled in the art.

4.3 Meshing of the Deformation Image

The meshing step applies a finite element method. The meshing allows spatial discretization of the body. The meshing consists of marking out in squares the deformation image (possibly segmented) via a plurality of elementary cells.

Each elementary cell delimits a medium with its own mechanical properties. Each elementary cell includes nodes and edges. A node may belong to several adjacent elementary cells. Also, an edge can only belong to two adjacent elementary cells.

4.4 Assigning Pairs of Unknown Variables to the Nodes of the Cells

As a reminder, the method allows determination of an elasticity image of a body according to the material(s) making up said body. The elasticities of the various materials (inclusions, etc.) making up the body are therefore unknown in any point of the deformation image. Rather than examining the elasticity in all the elementary cells of the body, a pair of unknown variables (known under the name of Lamé coefficients) ($\lambda_i$, $\mu_i$) representative of the elastic properties to be determined is associated with each node i of the elementary cells. Let us note that to each node i may be assigned either the Lamé coefficients ($\lambda_i$, $\mu_i$) or Young's modulus and the Poisson coefficient ($E_i$, $v_i$).

After having determined the values associated with these pairs of unknown variables at the nodes of the various elementary cells, it is possible to calculate the elastic properties inside the elementary cells with the help of a polynomial interpolation function. More specifically for a given elementary cell, when the values of the pairs of unknown variables were calculated at the nodes of the cell, it is possible to calculate pairs of unknown variables in any point inside the cell by interpolation from the pairs of unknown variables at the nodes of the cell. The fact of assigning pairs of unknown variables to the nodes of each elementary cell allows variation of the mechanical properties within the cell and will give the possibility of more finely reconstructing the elasticity mappings.

4.5 Detection and Enrichment

Once the pairs of unknown variables are assigned to the nodes of the elementary cells, the method comprises a step for detecting the nodes located at the boundary between two (or several) representative regions of areas in different materials of the body. An enrichment of the detected nodes is then carried out. For each detected node, the enrichment consists of replacing the pair of unknown nodal variables assigned to said common node detected by n enrichment pairs, "n" corresponding to the number of representative regions of areas of different materials.

Figure 3A:
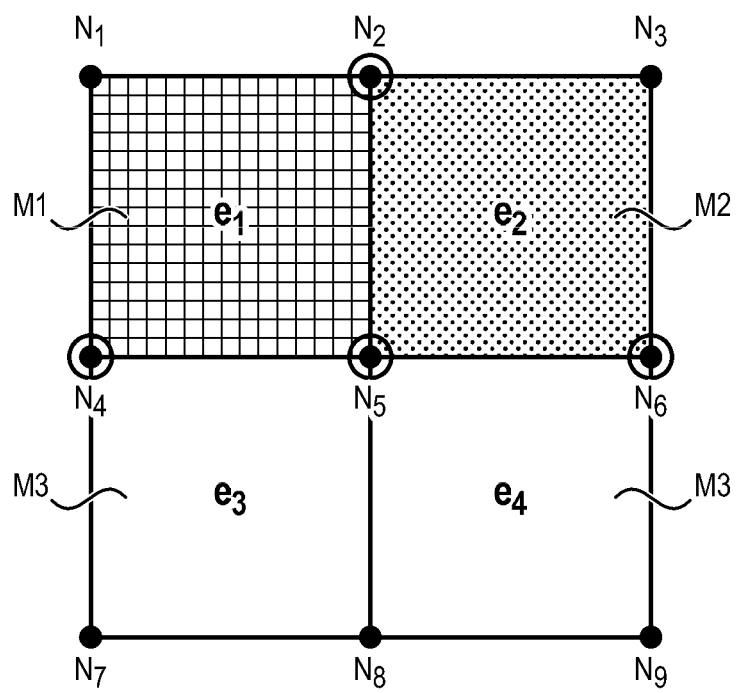
FIGS. 3A and 3B illustrate enriched (FIG. 3B) and non-enriched (FIG. 3A) elementary cells.
Figure 3B:
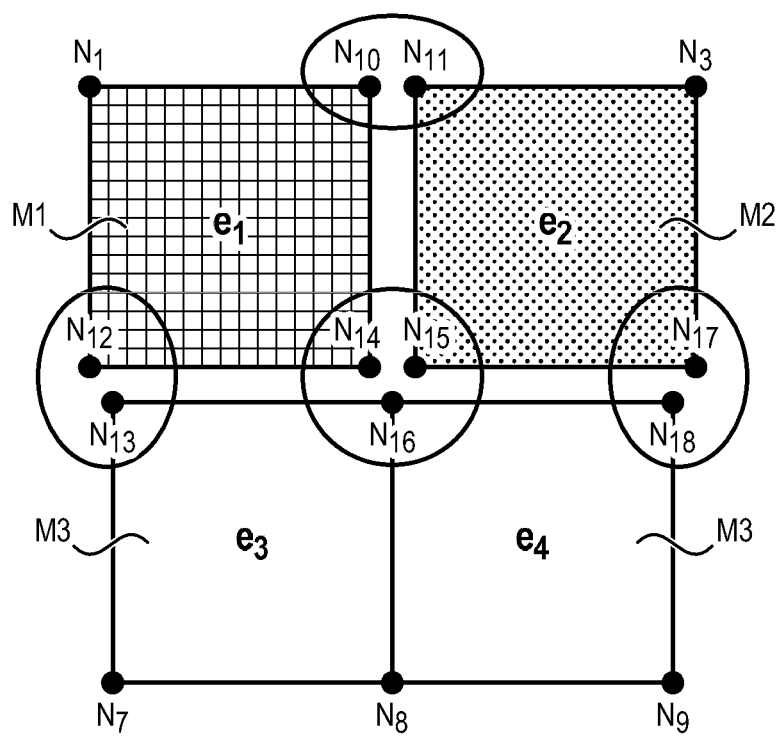

For example, if a detected node is located at the boundary between two regions, then the two unknown variables assigned to the node (a pair) are replaced by four (2×2) unknown variables (two pairs). If the detected node is located at the boundary of three regions, then the two unknown variables assigned to the node (a pair) are replaced with six (2×3) unknown variables (three pairs). If the detected node is located at the boundary of four regions, then the two unknown variables assigned to the node (a pair) are replaced with eight (2×4) unknown variables (four pairs), etc. The enrichment cases when the node is located at the boundary of two regions and three regions are illustrated in FIGS. 3A and 3B.

Each pair of unknown enrichment variables of the detected common node is associated with a respective elementary cell from among the adjacent elementary cells delimiting different materials. For example, in the case of a detected node N2 located at the boundary between two representative regions of areas of different materials M1, M2, then the first pair of enrichment variables is assigned to node N10 of the elementary cell delimiting a portion of the first region M1, and the second pair of enrichment variables is assigned to node N11 of the elementary cell delimiting a portion of the second region M2. In the case of a detected node N5 located at the boundary between three representative regions of areas of different materials M1, M2, M3, then a first pair of enrichment variables is assigned to the node N14 of the elementary cell delimiting a portion of the first region M1, a second pair of enrichment variables is assigned to the node N15 of the elementary cell delimiting a portion of the second region M2, and a third pair of enrichment variables is assigned to the common node N16 of the elementary cells delimiting a portion of the third region M3. The enrichment step (based on a principle similar to the XMEF method but reduced to the nodal mechanical properties of the elementary cells) gives the possibility of handling the discontinuities between the materials making up the studied body (in this case, the inclusions of the atheromatous plaque).

4.6 Calculation of the Elementary Matrices of the Cells and Assembling

Once the common nodes to several regions are enriched, the method comprises a step for calculating an elementary matrix for each elementary cell. This elementary matrix is calculated by taking into account the coordinates of the nodes, of the field of displacements (or deformations) to the nodes, and form functions used for the nodal constants of materials and of displacements. Two examples of calculations of elementary matrices are given in the Annex for a triangular elementary cell with 3 nodes and a rectangular elementary cell with 4 nodes.

When the elementary matrices have been calculated for all the elementary cells, the latter are assembled according to a standard assembling method used in the finite element method known to one skilled in the art. In this way a global structure matrix is obtained. This global matrix and the field of forces applied to the nodes are used for calculating the elasticities at the nodes of the different cells of the meshing. A map of the elasticities of the different materials making up the atheromatous plaque is thereby obtained. This elasticity map is then displayed (step 800) on display means such as a computer screen in order to allow a user to establish a diagnostic, and more specifically to identify the atheromatous plaques which may break.

Advantageously, the method described above may be implemented in program code so as to allow its application on a computer comprising a processor (configured for applying the steps of the method described above). This method gives the possibility from ultrasonic signals acquired by the user for example by IVUS, of displaying an elasticity map of an atheromatous plaque in real time on a display device of the computer. Theoretical aspects associated with the method according to the invention will now be described in more detail.

5. Theory

New Predictive Formulation of Calculating Structures with Finite Elements

In order to introduce the notion of enrichment of discontinuous material, the simple case of a plaque consisting of three distinct materials and meshed by using a meshing consisting of four elementary cells each including four nodes is considered subsequently (the illustration of this case is represented in FIGS. 3A and 3B). The representation with Galerkin finite elements of the elasticity equations applied to this structure is given in matrix form by:

$$[K(\lambda,\mu)]\{U\}=\{F\} \quad (1)$$

wherein:
{F} represents the nodal forces,
{U} represents the displacement vectors,
λ and μ are the Lamé coefficients associated with the properties of the materials of the cells, and
[K] is the global symmetrical rigidity matrix.

The approximations with finite elements of the displacements associated with a regular meshing as illustrated in FIGS. 3A and 3B are given by:

$$u(\vec{x}) = \sum_{i=N1}^{N9} u_i \varphi_i(\vec{x}) \text{ and } v(\vec{x}) = \sum_{i=N1}^{N9} v_i \varphi_i(\vec{x}) \quad (2a, b)$$

wherein:
u and v are the two components of the displacement vector,
$u_i$ and $v_i$ are the nodal displacements at node i,
$\varphi_i$ is the form function for the displacements associated with the node i and
$\vec{x}$ is the position vector.

The main challenges of this technique are the selection of the suitable nodes to be enriched, and the form of the associated enrichment form functions. The nodal enrichment method gives the possibility of satisfying the discontinuity constraint of the materials making up the atheromatous plaque by introducing additional nodes which increase the degrees of freedom of the nodes located at the boundary between two (or several) different materials of the atheromatous plaque. It was considered in the method according to the invention that one node has to be enriched if it is located at the boundary of material discontinuities.

FIGS. 3A and 3B illustrate the application of this rule on the simple example of the plaque. The nodes N2, N4, N5 and N6 have been enriched. Accordingly, the approximation by finite elements of the two material constants (i.e. the two Lamé coefficients λ and μ of the cells) associated with the meshing in FIGS. 3A and 3B is:

$$\lambda(\vec{x}) = \sum_{i\in I} \lambda_i \phi_i(\vec{x}) + \sum_{j\in J} \lambda_j \phi_j^*(\vec{x}) \quad (3a)$$

-continued $$\text{and } \mu(\vec{x}) = \sum_{i\in I} \mu_i \phi_i(\vec{x}) + \sum_{j\in J} \mu_j \phi_j^*(\vec{x}) \quad (3b)$$

with $$\phi_{10}^*(\vec{x}) = \begin{cases} \phi_2(\vec{x}) & \text{is} i \vec{x} \in e_1 \\ 0 & \text{otherwise} \end{cases} \quad \phi_{11}^*(\vec{x}) = \begin{cases} \phi_2(\vec{x}) & \text{si } \vec{x} \in e_2 \\ 0 & \text{otherwise} \end{cases} \quad (3c\text{-}e)$$

$$\phi_{12}^*(\vec{x}) = \begin{cases} \phi_4(\vec{x}) & \text{si } \vec{x} \in e_1 \\ 0 & \text{otherwise} \end{cases}$$

$$\phi_{13}^*(\vec{x}) = \begin{cases} \phi_4(\vec{x}) & \text{si } \vec{x} \in e_3 \\ 0 & \text{otherwise} \end{cases} \quad \phi_{14}^*(\vec{x}) = \begin{cases} \phi_5(\vec{x}) & \text{si } \vec{x} \in e_1 \\ 0 & \text{otherwise} \end{cases} \quad (3f\text{-}h)$$

$$\phi_{15}^*(\vec{x}) = \begin{cases} \phi_5(\vec{x}) & \text{si } \vec{x} \in e_2 \\ 0 & \text{otherwise} \end{cases}$$

$$\phi_{16}^*(\vec{x}) = \begin{cases} \phi_5(\vec{x}) & \text{si } \vec{x} \in e_3, e_4 \\ 0 & \text{otherwise} \end{cases} \quad \phi_{17}^*(\vec{x}) = \begin{cases} \phi_6(\vec{x}) & \text{si } \vec{x} \in e_2 \\ 0 & \text{otherwise} \end{cases} \quad (3i\text{-}k)$$

$$\phi_{18}^*(\vec{x}) = \begin{cases} \phi_6(\vec{x}) & \text{si } \vec{x} \in e_4 \\ 0 & \text{otherwise} \end{cases}$$

wherein:
$\varphi_i$ is the form function for the mechanical properties associated with node i and
$e_i$ (i=1 to 4) is the cell number,
I is the whole of the non-enriched nodes (i.e. I={nodes N1, N3, N7, N8 and N9}),
J is the set of all the relevant nodes at the location of the enriched nodes (i.e. J={nodes N10 to N18}) and
$\lambda_k$, $\mu_k$ (k∈I,J) are the components of the nodal material vectors {λ} and {μ} respectively.

Distinct form functions $\phi_i$ and $\varphi_i$ were used for the properties of the materials and of the displacement fields. For example a same geometry of an elementary cell may be considered with 3 nodes for the mechanical properties and with 6 nodes for the displacements. However, it is quite obvious to one skilled in the art that the form functions may be assume to be identical for the properties of the materials and the displacement fields.

New Formulation for Calculating Structures with Inverted Finite Elements

The equations of the predictive finite element method PMN-XFEM were rewritten by taking into account interpolation functions related to the nodal displacements (i.e. displacement at the node) and of interpolation functions related to the nodal mechanical properties of the materials. These same equations of the predictive finite element method PMN-XFEM were then reformulated so as to isolate the unknowns of the inverse elastography problem which are the nodal mechanical properties {R}. Thus, a displacement matrix [Q] was extracted and used for determining the mechanical properties at the nodes {R}. The following set of linear equilibrium equations is thereby obtained for the new methodology for calculating structures in the inverse finite element method:

$$[Q(u_k, v_k)]\{R\} = \{F\} \text{ with } \{R\} = \begin{bmatrix} \{\lambda\} \\ \{\mu\} \end{bmatrix} \quad (4)$$

The expression of the elementary displacement matrix $[Q^e]$ for a triangular mesh with 3 nodes and for a rectangular mesh with 4 nodes is given when the assumption of planar deformations is made (i.e. when the displacements of all the points of the plaque remain in the sectional plane) (cf. the Annex below). The elementary displacement matrix $[Q^e]$ is a square but not symmetrical matrix. In order to obtain the global displacement matrix $[Q]$, the displacement matrices of the different elementary cells $[Q^e]$ are assembled in a way known to one skilled in the art so as to infer therefrom the global rigidity matrix $[K]$, Numerical Resolution The global displacement matrix $[Q]$ is a rectangular matrix while the rigidity matrix $[K]$ is a square matrix. Theoretical aspects associated with the method according to the invention will now be described in more detail. The number of columns of the global displacement matrix $[Q]$ is equal to the sum of its number of lines and of twice the number of additional nodes at the enriched nodes. A similar system may be obtained by using nodal deformations instead of nodal displacement variables.

Considering the inverse problem, the matrix $[Q]$ is known since all the nodal displacements $u_k$ and $v_k$ are obtained from the deformation image illustrating the displacement field. The inverse problem is poorly conditioned because the nodal forces are not known on the nodes where the displacements have been imposed. The global force vector $\{F\}$ therefore has certain unknown components.

By suppressing the equations implying these unknown force components of the global finite element system, the reduced system of linear equations is obtained according to:

$$[Q'] \{R\} = \{F'\} \quad (5)$$

wherein:
$\{F'\}$ represents the reduced nodal force vector, and
$[Q']$ represents the reduced displacement matrix.

In order to solve this rectangular linear system, mathematical algorithms known to one skilled in the art are used. For example, a matrix product of the terms located on either side of the equality by the transposed matrix of the reduced displacement matrix; a square linear system is thus obtained:

$$[Q']^T[Q']\{R\} = [Q']^T\{F'\} \quad (6)$$

This system is then solved for determining the mechanical properties at the nodes $\{R\}$:

$$\{R\} = ([Q']^T[Q'])^{-1}[Q']^T\{F'\} \quad (7)$$

The method described above therefore gives the possibility of providing a real-time piece of information which may be utilized by the user allowing him/her to predict the risks of breakage of an atheromatous plaque.

6. Annexe 6.1 Expression of the Elementary Displacement Matrix $[Qe]$ when a Same Triangular Elementary Cell with 3 Nodes is Considered for the Mechanical Properties and Displacements The expression of the elementary displacement matrix $[Q^e]$ is provided here (which is a square and non-symmetrical matrix) for a triangular elementary cell with 3 nodes (1, 2 and 3) when the assumption of planar deformations is made (i.e. when the displacements of all the points of the plaque remain in the plane of the structure). Let $(x_i, y_i)$ and $(u_i, v_i)$ respectively be the coordinates and the displacements of the node $i$ (for $I=1$ to 3). The 36 components $Q_{ij}^e$ (i: line index; j: column index) of the non-symmetrical displacement square matrix (6 lines×6 columns) $[Q^e]$ are given below as a function of $xij$, $yij$ (wherein $xij=xj-xi$, $yij=yj-yi$ with $i, j=1$ to 3) and wherein A is the surface of a triangular elementary cell ($A=(x_{21}y_{31}-y_{21}x_{31})/2$):

Line 1

$Q_{11} = u_1 \cdot y_{23}^2 + v_1 \cdot x_{22} \cdot y_{23} + u_2 \cdot y_{31} \cdot y_{23} + v_2 \cdot x_{13} \cdot y_{23} + u_3 \cdot y_{12} \cdot y_{23} + v_3 \cdot x_{21} \cdot y_{23}$ $Q_{12} = u_1 \cdot (2y_{23}^2 + x_{23}^2) + v_1 \cdot x_{32} \cdot y_{23} + u_2 \cdot (2y_{31} \cdot y_{23} + x_{13} \cdot x_{32}) + v_2 \cdot x_{32} \cdot y_{31} + u_3 \cdot (2y_{12} \cdot y_{23} + x_{32} \cdot x_{21}) + v_3 \cdot x_{32} \cdot y_{12}$ $Q_{13} = u_1 \cdot y_{23}^2 + v_1 \cdot x_{22} \cdot y_{23} + u_2 \cdot y_{31} \cdot y_{23} + v_2 \cdot x_{13} \cdot y_{23} + u_3 \cdot y_{12} \cdot y_{23} + v_3 \cdot x_{21} \cdot y_{23}$ $Q_{14} = u_1 \cdot (2y_{23}^2 + x_{23}^2) + v_1 \cdot x_{32} \cdot y_{23} + u_2 \cdot (2y_{31} \cdot y_{23} + x_{13} \cdot x_{32}) + v_2 \cdot x_{32} \cdot y_{31} + u_3 \cdot (2y_{12} \cdot y_{23} + x_{32} \cdot x_{21}) + v_3 \cdot x_{32} \cdot y_{12}$ $Q_{15} = u_1 \cdot y_{23}^2 + v_1 \cdot x_{22} \cdot y_{23} + u_2 \cdot y_{31} \cdot y_{23} + v_2 \cdot x_{13} \cdot y_{23} + u_3 \cdot y_{12} \cdot y_{23} + v_3 \cdot x_{21} \cdot y_{23}$ $Q_{16} = u_1 \cdot (2y_{23}^2 + x_{23}^2) + v_1 \cdot x_{32} \cdot y_{23} + u_2 \cdot (2y_{31} \cdot y_{23} + x_{13} \cdot x_{32}) + v_2 \cdot x_{32} \cdot y_{31} + u_3 \cdot (2y_{12} \cdot y_{23} + x_{32} \cdot x_{21}) + v_3 \cdot x_{32} \cdot y_{12}$ Line 2

$Q_{21} = u_1 \cdot x_{32} \cdot y_{23} + v_1 \cdot x_{32}^2 + u_2 \cdot x_{32} \cdot y_{31} + v_2 \cdot x_{13} \cdot x_{32} + u_3 \cdot x_{32} \cdot y_{12} + v_3 \cdot x_{21} \cdot x_{32}$ $Q_{22} = u_1 \cdot x_{32} \cdot y_{23} + v_1 \cdot (2x_{32}^2 + y_{23}^2) + u_2 \cdot y_{23} \cdot x_{13} + v_2 \cdot (2 \cdot x_{32} x_{13} + y_{23} \cdot y_{31}) + u_3 \cdot x_{21} \cdot y_{23} + v_3 \cdot (2 \cdot x_{32} x_{21} + y_{12} \cdot y_{22})$ $Q_{23} = u_1 \cdot x_{32} \cdot y_{23} + v_1 \cdot x_{32}^2 + u_2 \cdot x_{32} \cdot y_{31} + v_2 \cdot x_{13} \cdot x_{32} + u_3 \cdot y_{12} \cdot x_{32} + v_3 \cdot x_{21} \cdot x_{32}$ $Q_{24} = u_1 \cdot x_{32} \cdot y_{23} + v_1 \cdot (2x_{32}^2 + y_{23}^2) + u_2 \cdot y_{23} \cdot x_{13} + v_2 \cdot (2 \cdot x_{32} x_{13} + y_{23} \cdot y_{31}) + u_3 \cdot x_{21} \cdot y_{23} + v_3 \cdot (2 \cdot x_{32} x_{21} + y_{12} \cdot y_{22})$ $Q_{25} = u_1 \cdot x_{32} \cdot y_{23} + v_1 \cdot x_{32}^2 + u_2 \cdot x_{32} \cdot y_{31} + v_2 \cdot x_{13} \cdot x_{32} + u_3 \cdot x_{32} \cdot y_{12} + v_3 \cdot x_{21} \cdot x_{32}$ $Q_{26} = u_1 \cdot x_{32} \cdot y_{23} + v_1 \cdot (2x_{32}^2 + y_{23}^2) + u_2 \cdot y_{23} \cdot x_{13} + v_2 \cdot (2 \cdot x_{32} x_{13} + y_{23} \cdot y_{31}) + u_3 \cdot x_{21} \cdot y_{23} + v_3 \cdot (2 \cdot x_{32} x_{21} + y_{12} \cdot y_{22})$ Line 3

$Q_{31} = u_1 \cdot y_{23} \cdot y_{31} + v_1 \cdot x_{32} \cdot y_{31} + u_2 \cdot y_{31}^2 + v_2 \cdot x_{13} \cdot y_{31} + u_3 \cdot y_{12} \cdot y_{31} + v_3 \cdot x_{21} \cdot y_{31}$ $Q_{32} = v_1 \cdot (2y_{23} \cdot y_{31} + x_{32} \cdot x_{13}) + v_1 \cdot x_{13} \cdot y_{23} + u_2 \cdot (2y_{31}^2 + x_{13}^2) + v_2 \cdot x_{13} \cdot y_{31} + u_3 \cdot (2y_{12} \cdot y_{31} + x_{13} \cdot x_{21}) + v_3 \cdot x_{13} \cdot y_{12}$ $Q_{33} = u_1 \cdot y_{23} \cdot y_{31} + v_1 \cdot x_{32} \cdot y_{31} + u_2 \cdot y_{31}^2 + v_2 \cdot x_{13} \cdot y_{31} + u_3 \cdot y_{12} \cdot y_{31} + v_3 \cdot x_{21} \cdot y_{31}$ $Q_{34} = v_1 \cdot (2y_{23} \cdot y_{31} + x_{32} \cdot x_{13}) + v_1 \cdot x_{13} \cdot y_{23} + u_2 \cdot (2y_{31}^2 + x_{13}^2) + v_2 \cdot x_{13} \cdot y_{31} + u_3 \cdot (2y_{12} \cdot y_{31} + x_{13} \cdot x_{21}) + v_3 \cdot x_{13} \cdot y_{12}$ $Q_{35} = u_1 \cdot y_{23} \cdot y_{31} + v_1 \cdot x_{32} \cdot y_{31} + u_2 \cdot y_{31}^2 + v_2 \cdot x_{13} \cdot y_{31} + u_3 \cdot y_{12} \cdot y_{31} + v_3 \cdot x_{21} \cdot y_{31}$ $Q_{36} = v_1 \cdot (2y_{23} \cdot y_{31} + x_{32} \cdot x_{13}) + v_1 \cdot x_{13} \cdot y_{23} + u_2 \cdot (2y_{31}^2 + x_{13}^2) + v_2 \cdot x_{13} \cdot y_{31} + u_3 \cdot (2y_{12} \cdot y_{31} + x_{13} \cdot x_{21}) + v_3 \cdot x_{13} \cdot y_{12}$ Line 4

$Q_{41} = u_1 \cdot x_{13} \cdot y_{23} + v_1 \cdot x_{13} \cdot x_{32} + u_2 \cdot x_{13} \cdot y_{31} + v_2 \cdot x_{13}^2 + u_3 \cdot x_{13} \cdot y_{12} + v_3 \cdot x_{21} \cdot x_{13}$ $Q_{42} = u_1 \cdot x_{32} \cdot y_{31} + v_1 \cdot (2x_{32} \cdot x_{13} + y_{23} \cdot y_{31}) + u_2 \cdot y_{31} \cdot x_{12} + v_2 \cdot (2 \cdot x_{13}^2 + y_{31}^2) + u_3 \cdot x_{21} \cdot y_{31} + v_3 \cdot (2 \cdot x_{13} x_{21} + y_{12} \cdot y_{31})$ $Q_{43} = u_1 \cdot x_{13} \cdot y_{23} + v_1 \cdot x_{13} \cdot x_{32} + u_2 \cdot x_{13} \cdot y_{31} + v_2 \cdot x_{13}^2 + u_3 \cdot x_{13} \cdot y_{12} + v_3 \cdot x_{21} \cdot x_{13}$ $Q_{44} = u_1 \cdot x_{32} \cdot y_{31} + v_1 \cdot (2x_{32} \cdot x_{13} + y_{23} \cdot y_{31}) + u_2 \cdot y_{31} \cdot x_{13} + v_2 \cdot (2 \cdot x_{13}^2 + y_{31}^2) + u_3 \cdot x_{21} \cdot y_{31} + v_3 \cdot (2 \cdot x_{13} x_{21} + y_{12} \cdot y_{31})$ $Q_{45} = u_1 \cdot x_{13} \cdot y_{23} + v_1 \cdot x_{13} \cdot x_{32} + u_2 \cdot x_{13} \cdot y_{31} + v_2 \cdot x_{13}^2 + u_3 \cdot x_{13} \cdot y_{12} + v_3 \cdot x_{21} \cdot x_{13}$ $Q_{46}=u_1 \cdot x_{32} \cdot y_{31}+v_1 \cdot (2x_{32} \cdot x_{13}+y_{23} \cdot y_{31})+u_2 \cdot y_{31} \cdot x_{12}+v_2 \cdot (2 \cdot x_{13}^2+y_{31}^2)+u_3 \cdot x_{21} \cdot y_{31}+v_3 \cdot (2 \cdot x_{13} \cdot x_{21}+y_{12} \cdot y_{31})$ Line 5

$Q_{51}=u_1 \cdot y_{12} \cdot y_{23}+v_1 \cdot x_{32} \cdot y_{12}+u_2 \cdot y_{31} \cdot y_{12}+v_2 \cdot x_{13} \cdot y_{12}+u_3 \cdot y_{12}^2+v_3 \cdot x_{21} \cdot y_{12}$ $Q_{52}=u_1 \cdot (2y_{23} \cdot y_{12}+x_{32} \cdot x_{21})+v_1 \cdot x_{21} \cdot y_{23}+u_2 \cdot (2y_{31} \cdot y_{12}+x_{13} \cdot x_{21})+v_2 \cdot x_{21} \cdot y_{31}+u_3 \cdot (2y_{12}^2+x_{21}^2)+v_3 \cdot x_{13} \cdot y_{12}$ $Q_{53}=u_1 \cdot y_{12} \cdot y_{23}+v_1 \cdot x_{32} \cdot y_{12}+u_2 \cdot y_{31} \cdot y_{12}+v_2 \cdot x_{13} \cdot y_{12}+u_3 \cdot y_{12}^2+v_3 \cdot x_{21} \cdot y_{12}$ $Q_{54}=u_1 \cdot (2y_{23} \cdot y_{12}+x_{32} \cdot x_{21})+v_1 \cdot x_{21} \cdot y_{23}+u_2 \cdot (2y_{31} \cdot y_{12}+x_{13} \cdot x_{21})+v_2 \cdot x_{21} \cdot y_{31}+u_3 \cdot (2y_{12}^2+x_{21}^2)+v_3 \cdot x_{13} \cdot y_{12}$ $Q_{55}=u_1 \cdot y_{12} \cdot y_{23}+v_1 \cdot x_{32} \cdot y_{12}+u_2 \cdot y_{31} \cdot y_{12}+v_2 \cdot x_{13} \cdot y_{12}+u_3 \cdot y_{12}^2+v_3 \cdot x_{21} \cdot y_{12}$ $Q_{56}=u_1 \cdot (2y_{23} \cdot y_{12}+x_{32} \cdot x_{21})+v_1 \cdot x_{21} \cdot y_{23}+u_2 \cdot (2y_{31} \cdot y_{12}+x_{13} \cdot x_{21})+v_2 \cdot x_{21} \cdot y_{31}+u_3 \cdot (2y_{12}^2+x_{21}^2)+v_3 \cdot x_{13} \cdot y_{12}$ Line 6

$Q_{61}=u_1 \cdot x_{21} \cdot y_{23}+v_1 \cdot x_{21} \cdot x_{32}+u_2 \cdot x_{21} \cdot y_{31}+v_2 \cdot x_{13} \cdot x_{21}+u_3 \cdot x_{21} \cdot y_{12}+v_3 \cdot x_{21}^2$ $Q_{62}=u_1 \cdot x_{32} \cdot y_{12}+v_1 \cdot (2x_{32} \cdot x_{21}+y_{23} \cdot y_{12})+u_2 \cdot y_{12} \cdot x_{13}+v_2 \cdot (2 \cdot x_{13} \cdot x_{21}+y_{31} \cdot y_{12})+y_3 \cdot x_{21} \cdot y_{12}+v_2 \cdot (2x_{21}^2+y_{12}^2)$ $Q_{63}=u_1 \cdot x_{21} \cdot y_{23}+v_1 \cdot x_{21} \cdot x_{32}+u_2 \cdot x_{21} \cdot y_{31}+v_2 \cdot x_{13} \cdot x_{21}+u_3 \cdot x_{21} \cdot y_{12}+v_3 \cdot x_{21}^2$ $Q_{64}=u_1 \cdot x_{32} \cdot y_{12}+v_1 \cdot (2x_{32} \cdot x_{21}+y_{23} \cdot y_{12})+u_2 \cdot y_{12} \cdot x_{13}+v_2 \cdot (2 \cdot x_{13} \cdot x_{21}+y_{31} \cdot y_{12})+y_3 \cdot x_{21} \cdot y_{12}+v_2 \cdot (2x_{21}^2+y_{12}^2)$ $Q_{65}=u_1 \cdot x_{21} \cdot y_{23}+v_1 \cdot x_{21} \cdot x_{32}+u_2 \cdot x_{21} \cdot y_{31}+v_2 \cdot x_{13} \cdot x_{21}+u_3 \cdot x_{21} \cdot y_{12}+v_3 \cdot x_{21}^2$ $Q_{66}=u_1 \cdot x_{32} \cdot y_{12}+v_1 \cdot (2x_{32} \cdot x_{21}+y_{23} \cdot y_{12})+u_2 \cdot y_{12} \cdot x_{13}+v_2 \cdot (2 \cdot x_{13} \cdot x_{21}+y_{31} \cdot y_{12})+y_3 \cdot x_{21} \cdot y_{12}+v_2 \cdot (2x_{21}^2+y_{12}^2)$

6.2 Expression of the Elementary Displacement Matrix [Qe] when a Same Rectangular Elementary Cell with 4 Nodes is Considered for the Mechanical Properties and the Displacements The expression of the elementary displacement matrix $[Q^e]$ is provided here (which is a square and non-symmetrical matrix) for a rectangular elementary cell with 4 nodes (1, 2, 3 and 4 of respective coordinates (−a,−b), (a,−b), (a,b) and (−a,b)) when the assumption of planar deformations is made (i.e. when the displacements of all the points of the plaque remain in the plane of the structure). Let (ui, vi) be the displacements of the node i (for i=1 to 4). The 64 components $Q_{ij}^e$ (i: line index; j: column index) of the non-symmetrical displacement square matrix (8 lines×8 columns) $[Q^e]$ are given below.

Line 1

$Q_{11} = \frac{1}{24a}(3u_1 - 3u_2 - u_3 + u_4) + \frac{1}{18}(2v_1 + v_2 - v_3 - 2v_4)$ $Q_{12} = \frac{1}{24ab}[(3a^2 + 6b^2)u_1 + (a^2 - 6b^2)u_2 - (a^2 + 2b^2)u_3 - (3a^2 - 2b^2)u_4] + \frac{1}{18}(2v_1 - 2v_2 - v_3 + v_4)$ $Q_{13} = \frac{1}{24a}(3u_1 - 3u_2 - u_3 + u_4) + \frac{1}{18}(v_1 + 2v_2 - 2v_3 - v_4)$ $Q_{14} = \frac{1}{24ab}[(a^2 + 6b^2)u_1 + (a^2 - 6b^2)u_2 - (a^2 + 2b^2)u_3 - (a^2 - 2b^2)u_4] + \frac{1}{36}(2v_1 - 2v_2 - v_3 + v_4)$ $Q_{15} = \frac{1}{24a}(u_1 - u_2 - u_3 + u_4) + \frac{1}{36}(v_1 + 2v_2 - 2v_3 - v_4)$ $Q_{16} = \frac{1}{24ab}[(a^2 + 2b^2)u_1 + (a^2 - 2b^2)u_2 - (a^2 + 2b^2)u_3 - (a^2 - 2b^2)u_4] + \frac{1}{36}(v_1 - v_2 - 2v_3 + 2v_4)$ $Q_{17} = \frac{1}{24a}(u_1 - u_2 - u_3 + u_4) + \frac{1}{36}(2v_1 + v_2 - 2v_3 - 2v_4)$ $Q_{18} = \frac{1}{24ab}[(3a^2 + 2b^2)u_1 + (a^2 - 2b^2)u_2 - (a^2 + 2b^2)u_3 - (3a^2 - 2b^2)u_4] + \frac{1}{18}(v_1 - v_2 - 2v_3 + 2v_4)$ Line 2

$Q_{21} = \frac{1}{18}(2u_1 - 2u_2 - u_3 + u_4) + \frac{a}{24b}(3v_1 + v_2 - v_3 - 3v_4)$ $Q_{22} = \frac{1}{18}(2u_1 + u_2 - u_3 - 2u_4) + \frac{1}{24ab}[(6a^2 + 3b^2)v_1 + (2a^2 - 3b^2)v_2 - (2a^2 + b^2)v_3 - (6a^2 - b^2)v_4]$ $Q_{23} = \frac{1}{36}(2u_1 - 2u_2 - u_3 + u_4) + \frac{a}{24b}(v_1 + v_2 - v_3 - v_4)$ $Q_{24} = \frac{1}{18}(2u_1 + u_2 - u_3 - 2u_4) + \frac{1}{24ab}[(2a^2 + 3b^2)v_1 + (2a^2 - 3b^2)v_2 - (2a^2 + b^2)v_3 - (2a^2 - b^2)v_4]$ $Q_{25} = \frac{1}{36}(u_1 - u_2 - 2u_3 + 2u_4) + \frac{a}{24b}(v_1 + v_2 - v_3 - v_4)$ $Q_{26} = \frac{1}{36}(u_1 + 2u_2 - 2u_3 - u_4) + \frac{1}{24ab}[(2a^2 + b^2)v_1 + (2a^2 - b^2)v_2 - (2a^2 + b^2)v_3 - (2a^2 - b^2)v_4]$ $Q_{27} = \frac{1}{18}(u_1 - u_2 - 2u_3 + 2u_4) + \frac{a}{24b}(3v_1 + v_2 - v_3 - 3v_4)$ $Q_{28} = \frac{1}{36}(2u_1 + u_2 - u_3 - 2u_4) + \frac{1}{24ab}[(6a^2 + b^2)v_1 + (2a^2 - b^2)v_2 - (2a^2 + b^2)v_3 - (6a^2 - b^2)v_4]$ Line 3

$Q_{31} = \frac{b}{24a}(-3u_1 + 3u_2 + u_3 - u_4) + \frac{1}{18}(-2v_1 - v_2 + v_3 + 2v_4)$ $Q_{32} = \frac{1}{24ab}[(a^2 - 6b^2)u_1 + (a^2 + 6b^2)u_2 - (a^2 - 2b^2)u_3 - (a^2 + 2b^2)u_4] + \frac{1}{36}(2v_1 - 2v_2 - v_3 + v_4)$ $Q_{33} = \frac{b}{24a}(-3u_1 + 3u_2 + u_3 - u_4) + \frac{1}{18}(-v_1 - 2v_2 + 2v_3 + v_4)$ $Q_{34} = \frac{1}{24ab}[(a^2 - 6b^2)u_1 + (3a^2 + 6b^2)u_2 - (3a^2 - 2b^2)u_3 - (a^2 + 2b^2)u_4] + \frac{1}{18}(2v_1 - 2v_2 - v_3 + v_4)$ $Q_{35} = \frac{b}{24a}(-u_1 + u_2 + u_3 - u_4) + \frac{1}{36}(-v_1 - 2v_2 + 2v_3 + v_4)$ $Q_{36} = \frac{1}{24ab}[(a^2 - 2b^2)u_1 + (3a^2 + 2b^2)u_2 - (3a^2 - 2b^2)u_3 - (a^2 + 2b^2)u_4] +$ $$Q_{37} = \frac{b}{24a}(-u_1 + u_2 + u_3 - u_4) + \frac{1}{36}(-2v_1 - v_2 + v_3 + 2v_4)$$

$$Q_{38} = \frac{1}{24ab}[(a^2 - 2b^2)u_1 + (a^2 + 2b^2)u_2 - (a^2 - 2b^2)u_3 - (a^2 + 2b^2)u_4] + \frac{1}{36}(v_1 - v_2 - 2v_3 + 2v_4)$$

Line 4

$$Q_{41} = \frac{1}{36}(2u_1 - 2u_2 - u_3 + u_4) + \frac{a}{24b}(v_1 + v_2 - v_3 - v_4)$$

$$Q_{42} = \frac{1}{18}(-2u_1 - u_2 + u_3 + 2u_4) + \frac{1}{24ab}[2a^2 - 3b^2)v_1 + (2a^2 + 3b^2)v_2 - (2a^2 - b^2)v_3 - (2a^2 + b^2)v_4]$$

$$Q_{43} = \frac{1}{18}(2u_1 - 2u_2 - u_3 + u_4) + \frac{a}{24b}(v_1 + 3v_2 - 3v_3 - v_4)$$

$$Q_{44} = \frac{1}{18}(-u_1 - 2u_2 + 2u_3 + u_4) + \frac{1}{24ab}[(2a^2 - 3b^2)v_1 + (2a^2 + b^2)v_2 - (6a^2 - b^2)v_3 - (2a^2 + b^2)v_4]$$

$$Q_{45} = \frac{1}{18}(u_1 - u_2 - 2u_3 + 2u_4) + \frac{a}{24b}(v_1 + 3v_2 - 3v_3 - v_4)$$

$$Q_{46} = \frac{1}{36}(-u_1 - 2u_2 + 2u_3 + u_4) + \frac{1}{24ab}[(2a^2 - b^2)v_1 + (6a^2 + b^2)v_2 - (6a^2 - b^2)v_3 - (2a^2 + b^2)v_4]$$

$$Q_{47} = \frac{1}{36}(u_1 - u_2 - 2u_3 + 2u_4) + \frac{a}{24b}(v_1 + v_2 - v_3 - v_4)$$

$$Q_{48} = \frac{1}{36}(-2u_1 - u_2 + u_3 + 2u_4) + \frac{1}{24ab}[(2a^2 - b^2)v_1 + (2a^2 + b^2)v_2 - (2a^2 - b^2)v_3 - (2a^2 + b^2)v_4]$$

Line 5

$$Q_{51} = \frac{b}{24a}(-u_1 + u_2 + u_3 - u_4) + \frac{1}{36}(-2v_1 - v_2 + v_3 + 2v_4)$$

$$Q_{52} = \frac{1}{24ab}[-(a^2 + 2b^2)u_1 - (a^2 - 2b^2)u_2 + (a^2 + 2b^2)u_3 + (a^2 - 2b^2)u_4] + \frac{1}{36}(-2v_1 + 2v_2 + v_3 - v_4)$$

$$Q_{53} = \frac{b}{24a}(-u_1 + u_2 + u_3 - u_4) + \frac{1}{36}(-v_1 - 2v_2 + 2v_3 + v_4)$$

$$Q_{54} = \frac{1}{24ab}[-(a^2 + 2b^2)u_1 - (3a^2 - 2b^2)u_2 + (3a^2 + 2b^2)u_3 + (a^2 + 2b^2)u_4] + \frac{1}{18}(-2v_1 + 2v_2 + v_3 - v_4)$$

$$Q_{55} = \frac{b}{24a}(-u_1 + u_2 + 3u_3 - 3u_4) + \frac{1}{18}(-v_1 - 2v_2 + 2v_3 + v_4)$$

$$Q_{56} = \frac{1}{24ab}[-(a^2 - 2b^2)u_1 - (3a^2 - 2b^2)u_2 + (a^2 + 2b^2)u_3 + (a^2 - 6b^2)u_4] + \frac{1}{18}(-v_1 + v_2 + 2v_3 - 2v_4)$$

$$Q_{57} = \frac{b}{24a}(-u_1 + u_2 + 3u_3 - 3u_4) + \frac{1}{18}(-2v_1 - v_2 + v_3 + 2v_4)$$

$$Q_{58} = \frac{1}{24ab}[-(a^2 + 2b^2)u_1 - (a^2 - 2b^2)u_2 + (a^2 + 6b^2)u_3 + (a^2 - 6b^2)u_4] + \frac{1}{36}(-v_1 + v_2 + 2v_3 - 2v_4)$$

Line 6

$$Q_{61} = \frac{1}{36}(-2u_1 + 2u_2 + u_3 - u_4) + \frac{a}{24b}(-v_1 - v_2 + v_3 + v_4)$$

$$Q_{62} = \frac{1}{36}(-2u_1 - u_2 + u_3 + 2u_4) + \frac{1}{24ab}[-(2a^2 + b^2)v_1 - (2a^2 - b^2)v_2 + (2a^2 + b^2)v_3 + (2a^2 - b^2)v_4]$$

$$Q_{63} = \frac{1}{18}(-2u_1 + 2u_2 + u_3 - u_4) + \frac{a}{24b}(-v_1 - 3v_2 + 3v_3 + v_4)$$

$$Q_{64} = \frac{1}{36}(-u_1 - 2u_2 + 2u_3 + u_4) + \frac{1}{24ab}[-(2a^2 + b^2)v_1 - (6a^2 - b^2)v_2 + (6a^2 + b^2)v_3 + (2a^2 - b^2)v_4]$$

$$Q_{65} = \frac{1}{18}(-u_1 + u_2 + 2u_3 - 2u_4) + \frac{a}{24b}(-v_1 - 3v_2 + 3v_3 + v_4)$$

$$Q_{66} = \frac{1}{18}(-u_1 - 2u_2 + 2u_3 + u_4) + \frac{1}{24ab}[-(2a^2 + b^2)v_1 - (6a^2 - b^2)v_2 + (2a^2 + b^2)v_3 + (2a^2 - 3b^2)v_4]$$

$$Q_{67} = \frac{1}{36}(-u_1 + u_2 + 2u_3 - 2u_4) + \frac{a}{24b}(-v_1 - v_2 + v_3 + v_4)$$

$$Q_{68} = \frac{1}{18}(-2u_1 - u_2 + u_3 + 2u_4) + \frac{1}{24ab}[-(2a^2 + b^2)v_1 - (2a^2 - b^2)v_2 + (2a^2 + 3b^2)v_3 + (2a^2 - 3b^2)v_4]$$

Line 7

$$Q_{71} = \frac{b}{24a}(u_1 - u_2 - u_3 + u_4) + \frac{1}{36}(2v_1 v_2 - v_3 - 2v_4)$$

$$Q_{72} = \frac{1}{24ab}[-(3a^2 - 2b^2)u_1 - (a^2 + 2b^2)u_2 + (a^2 - 2b^2)u_3 + (3a^2 + 2b^2)u_4] + \frac{1}{18}(-2v_1 + 2v_2 + v_3 - v_4)$$

$$Q_{73} = \frac{b}{24a}(u_1 - u_2 - u_3 - u_4) + \frac{1}{36}(v_1 + 2v_2 - 2v_3 - v_4)$$

$$Q_{74} = \frac{1}{24ab}[-(a^2 - 2b^2)u_1 - (a^2 + 2b^2)u_2 + (a^2 - 2b^2)u_3 + (a^2 + 2b^2)u_4] + \frac{1}{36}(-2v_1 + 2v_2 + v_3 - v_4)$$

$$Q_{75} = \frac{b}{24a}(u_1 - u_2 - 3u_3 + 3u_4) + \frac{1}{18}(v_1 + 2v_2 - 2v_3 - v_4)$$

$$Q_{76} = \frac{1}{24ab}[-(a^2 - 2b^2)u_1 - (a^2 + 2b^2)u_2 + (a^2 - 6b^2)u_3 + (a^2 + 6b^2)u_4] + \frac{1}{36}(-v_1 + v_2 + 2v_3 - 2v_4)$$

$$Q_{77} = \frac{b}{24a}(u_1 - u_2 - 3u_3 + 3u_4) + \frac{1}{18}(2v_1 + v_2 - v_3 - 2v_4)$$

$$Q_{78} =$$

-continued $$\frac{1}{24ab}[-(3a^2+2b^2)u_1-(a^2+2b^2)u_2+(a^2-6b^2)u_3+(a^2+2b^2)u_4]+$$

$$\frac{1}{18}(-v_1+v_2+2v_3-2v_4)$$

Line 8

$$Q_{81}=\frac{1}{18}(-2u_1+2u_2+u_3-u_4)+\frac{a}{24b}(-3v_1-v_2+v_3+3v_4)$$

$$Q_{82}=\frac{1}{36}(2u_1+u_2-u_3-2u_4)+$$

$$\frac{1}{24ab}[-(6a^2-b^2)v_1-(2a^2+b^2)v_2+(2a^2-b^2)v_3+(6a^2+b^2)v_4]$$

$$Q_{83}=\frac{1}{36}(-2u_1+2u_2+u_3-u_4)+\frac{a}{24b}(-v_1-v_2+v_3+v_4)$$

$$Q_{84}=\frac{1}{36}(u_1+2u_2-2u_3-u_4)+$$

$$\frac{1}{24ab}[-(2a^2-b^2)v_1-(2a^2+b^2)v_2+(2a^2-b^2)v_3+(2a^2+b^2)v_4]$$

$$Q_{85}=\frac{1}{36}(-u_1+u_2+2u_3-2u_4)+\frac{a}{24b}(-v_1-v_2+v_3+v_4)$$

$$Q_{86}=\frac{1}{18}(u_1+2u_2-2u_3-u_4)+$$

$$\frac{1}{24ab}[-(2a^2-b^2)v_1-(2a^2+b^2)v_2+(2a^2-3b^2)v_3+(2a^2+3b^2)v_4]$$

$$Q_{87}=\frac{1}{18}(-u_1+u_2+2u_3-2u_4)+\frac{a}{24b}(-3v_1-v_2+v_3+3v_4)$$

$$Q_{88}=\frac{1}{18}(2u_1+u_2-u_3-2u_4)+$$

$$\frac{1}{24ab}[-(6a^2-b^2)v_1-(2a^2+b^2)v_2+(2a^2-3b^2)v_3+(2a^2+b^2)v_4]$$

BIBLIOGRAPHIC REFERENCES

Doyley M M. Model-based elastography: a survey of approaches to the inverse elasticity problem. Phys Med Biol 2012; 57:R35-73.

Le Floc'h S, Ohayon J, Tracqui P, Finet G, Gharib A M, Maurice R L, Cloutier G, Pettigrew R I. Vulnerable atherosclerotic plaque elasticity reconstruction based on a segmentation-driven optimization procedure using strain measurements: theoretical framework. IEEE Trans Med Imaging 2009; 28: 1126-37.

Moës N, Dolbow J, Belytschko T. A finite element method for crack growth without remeshing. Int J Numer Meth Engng 1999; 46: 131-50

Oberai A A, Gokhale N H, Feijoo G R. Solution of inverse problems in elasticity imaging using the adjoint method. Inverse Problems 2003; 19: 297-313.

Zhu Y, Hall T J, Jiang J. A finite-element approach for Young's modulus reconstruction. IEEE Trans Med Imaging 2003; 22: 890-901.

The invention claimed is:

1. A method for image processing for formation of an elasticity image of a body, the method comprising the steps of:
receiving a deformation image illustrating a displacement or deformation field of the points of the body as a function of a pressure difference in the body, wherein the deformation image is a deformation elastogram produced by introducing an ultrasonic wave into the body;
defining a meshing of the deformation image, the meshing step applying a finite element method, the meshing including a plurality of elementary cells each delimiting a same material and each including at least three nodes, each node belonging to one or several adjacent cells to the meshing;
assigning to each node i of the meshing a pair of unknown nodal variables, each pair being representative of elastic properties to be determined;
detecting at least one node common to at least two adjacent elementary cells delimiting different materials;
enriching the at least one detected common node the enrichment step including replacing the pair of unknown variables assigned to the detected common node with at least two pairs of enrichment unknown variables, each pair of enrichment unknown variables of the detected common node being assigned to a respective elementary cell from among the at least two adjacent elementary cells delimiting different materials;
calculating an elementary matrix for each elementary cell of the meshing so as to obtain a plurality of elementary matrices, the elementary matrices being calculated by taking into account pairs of unknown variables assigned to the elementary cells, and pairs of unknown variables assigned to the elementary cells;
assembling the elementary matrices of the plurality of elementary matrices in order to obtain a structure matrix;
calculating the elasticity image of the body from the deformation image and from the structure matrix; and
displaying the elasticity image.

2. The method according to claim 1, further comprising, prior to the step of defining a meshing, a step consisting of segmenting the deformation image in order to obtain a segmented deformation image including a plurality of representative regions of areas of the body assumed to be in different materials.

3. The method according to claim 2, wherein the step of defining a meshing is applied on the segmented deformation image, the dimensions and positions of the cells of the meshing being determined depending on the positions and dimensions of the regions of the segmented deformation image.

4. The method according to claim 1, wherein the step of calculating an elasticity image comprises the resolution of the following matrix equation:

$$\{R\}=([Q']^T[Q'])^{-1}[Q']^T\{F'\}$$

wherein:
[Q'] represents the reduced structure matrix, and [Q']$^T$ its transposed,
{F'} represents the reduced matrix of the field of forces applied to the nodes, and
{R} represents the matrix of the field of elasticities of the body at the nodes.

5. The method according to claim 1, wherein the step of enriching a detected common node comprises the replacement of the pair of unknown variables assigned to the common node detected by n pairs of enrichment unknown variables, n corresponding to the number of different materials at the boundary of which is located the common node.

6. A system for image processing for formation of an elasticity image of a body, the system comprising:
a receiver for receiving a deformation image illustrating a displacement field of the points of the body as a function of a pressure difference in the body, wherein the deformation image is a deformation elastogram produced by introducing an ultrasonic wave into the body;

a processor configured to:
define a meshing of the deformation image by applying a finite element method, the meshing consisting of a plurality of elementary cells each delimiting a same material and each including at least three nodes, each node belonging to one or several cells adjacent to the meshing;
assign to each node i of the meshing a pair of unknown nodal variables (($\lambda_i$, $\mu_i$) or ($E_1$, $v_i$)), each pair being representative of elastic properties to be determined;
detect at least one node common to at least two adjacent elementary cells delimiting different materials;
enrich the and at least one detected common node, the enrichment including replacing the pair of unknown variables assigned to the detected common node with at least two pairs of unknown enrichment variables, each pairs of unknown enrichment variables of the detected common node being assigned to a respective elementary cell from among the at least two adjacent elementary cells delimiting different materials;
calculate an elementary matrix for each elementary cell of the meshing so as to obtain a plurality of elementary matrices, the elementary matrices being calculated while taking into account pairs of unknown variables assigned to the elementary cells, and pairs of unknown variables assigned to the elementary cells;
assemble the elementary matrices from the plurality of elementary matrices for obtaining a structure matrix; and
calculate the elasticity image of the body from the deformation image and from the structure matrix; and
a display device,
wherein the processor is further configured to display the elasticity image on the display device.

7. The system according to claim 6, wherein the processor is configured to segment the deformation image in order to obtain a segmented deformation image consisting of a plurality of representative regions of areas of the body assumed to be in different materials.

8. A computer program product for executing image processing for formation of an elasticity image of a body comprising a non-transitory computer readable medium storing instructions that, when executed by a computer, cause the computer to perform operations comprising:
receiving a deformation image illustrating a displacement or deformation field of the points of the body as a function of a pressure difference in the body, wherein the deformation image is a deformation elastogram produced by introducing an ultrasonic wave into the body;
defining a meshing of the deformation image, the meshing step applying a finite element method, the meshing including a plurality of elementary cells each delimiting a same material and each including at least three nodes, each node belonging to one or several adjacent cells to the meshing;
assigning to each node i of the meshing a pair of unknown nodal variables, each pair being representative of elastic properties to be determined;
detecting at least one node common to at least two adjacent elementary cells delimiting different materials;
enriching the at least one detected common node, the enrichment step including replacing the pair of unknown variables assigned to the detected common node with at least two pairs of enrichment unknown variables, each pair of enrichment unknown variables of the detected common node being assigned to a respective elementary cell from among the at least two adjacent elementary cells delimiting different materials;
calculating an elementary matrix for each elementary cell of the meshing so as to obtain a plurality of elementary matrices, the elementary matrices being calculated by taking into account pairs of unknown variables assigned to the elementary cells, and pairs of unknown variables assigned to the elementary cells;
assembling the elementary matrices of the plurality of elementary matrices in order to obtain a structure matrix; and
calculating the elasticity image of the body from the deformation image and from the structure matrix; and
displaying the elasticity image.

* * * * *